US011510796B2

(12) United States Patent
Garcia Torres et al.

(10) Patent No.: US 11,510,796 B2
(45) Date of Patent: Nov. 29, 2022

(54) HORSESHOE-SHAPED GUIDE CATHETER AND PROCEDURE FOR DUCTUS ARTERIOSUS ANGIOPLASTY IN NEWBORN AND INFANT PATIENTS

(71) Applicants: FUNDACION CARDIOINFANTIL, Bogota (CO); UNIVERSIDAD DE LOS ANDES, Bogota (CO); Alberto Enrique Garcia Torres, Bogota (CO); Juan Carlos Briceno Triana, Bogota (CO); Juliana Sanchez Posada, Bogota (CO)

(72) Inventors: Alberto Enrique Garcia Torres, Bogota (CO); Juan Carlos Briceno Triana, Bogota (CO); Juliana Sanchez Posada, Bogota (CO)

(73) Assignees: FUNDACION CARDIOINFANTIL, Bogota (CO); UNIVERSIDAD DE LOS ANDES, Bogota (CO); Alberto Enrique Garcia Torres, Bogota (CO); Juan Carlos Briceno Triana, Bogota (CO); Juliana Sanchez Posada, Bogota (CO)

( * ) Notice: Subject to any disclaimer, the term of this patent is extended or adjusted under 35 U.S.C. 154(b) by 534 days.

(21) Appl. No.: 16/305,767

(22) PCT Filed: Jun. 2, 2017

(86) PCT No.: PCT/IB2017/053276
§ 371 (c)(1),
(2) Date: Nov. 29, 2018

(87) PCT Pub. No.: WO2017/208202
PCT Pub. Date: Dec. 7, 2017

(65) Prior Publication Data
US 2020/0323667 A1 Oct. 15, 2020

(30) Foreign Application Priority Data
Jun. 3, 2016 (CO) .................................. 16-146226

(51) Int. Cl.
*A61F 2/958* (2013.01)
*A61F 2/82* (2013.01)
*A61M 25/10* (2013.01)

(52) U.S. Cl.
CPC ................ *A61F 2/958* (2013.01); *A61F 2/82* (2013.01); *A61M 25/104* (2013.01); *A61F 2230/0013* (2013.01); *A61F 2250/0082* (2013.01)

(58) Field of Classification Search
CPC .... A61F 2/958; A61F 2/82; A61F 2/95; A61F 2230/0013; A61F 2250/0082; A61F 2/90;
(Continued)

(56) References Cited

U.S. PATENT DOCUMENTS 2,118,631 A   5/1938  Wappler
4,212,304 A   7/1980  Finney
(Continued)

FOREIGN PATENT DOCUMENTS

CO      15183571 A    1/2016
CO      15183571 A1   1/2016
(Continued)

OTHER PUBLICATIONS

Alwi, Mazeni, et al. "Initial results and medium-term follow-up of stent implantation of patent ductus arteriosus in duct-dependent pulmonary circulation." Journal of the American College of Cardiology 44.2 (Jul. 21, 2004): 438-445. (Year: 2004).*
(Continued)

*Primary Examiner* — Yashita Sharma
(74) *Attorney, Agent, or Firm* — Lucas & Mercanti, LLP

(57) ABSTRACT

A horseshoe-shaped guide catheter for stent angioplasty of the ductus arteriosus in newborn and infants with ductal-
(Continued)

dependent cardiopathies, characterized by a long, straight, hollow first section merged at the distal end thereof to a second section formed by a curved portion shaped as a circle section with radius (Ra) of 7.5 mm to 9 mm, arc (b) of 180° to 280° and distance (d) between the tip of the second section and the straight part of the first section without deformations of 7 mm and 15 mm. The angioplasty makes it possible to insert one or more stents that keep the ductus open in extrauterine life, improving survival of the newborn and young infants, allowing weight gain and undergo corrective surgery a few months later with safer and with better outcomes.

4 Claims, 8 Drawing Sheets

(58) Field of Classification Search
CPC ............... A61M 25/00; A61M 25/104; A61M 2210/125; A61M 25/0041; A61M 25/0662; A61M 2240/00; A61B 2017/00292; A61B 2017/00243
See application file for complete search history.

(56) References Cited

U.S. PATENT DOCUMENTS

| | | | |
|---|---|---|---|
| 4,610,657 A | | 9/1986 | Densow |
| 4,747,840 A | | 5/1988 | Ladika et al. |
| 4,790,810 A | | 12/1988 | Pugh, Jr. et al. |
| 4,931,037 A | | 6/1990 | Wetterman |
| 5,261,878 A | | 11/1993 | Galindo |
| 5,445,625 A | * | 8/1995 | Voda ................. A61M 25/0041 604/523 |
| 5,531,741 A | | 7/1996 | Barbacci |
| 10,335,577 B2 | * | 7/2019 | Fulton, III ........ A61M 25/0084 |
| 10,434,287 B2 | * | 10/2019 | Merkel ............. A61M 25/0041 |
| 2004/0015151 A1 | | 1/2004 | Chambers |
| 2009/0204198 A1 | * | 8/2009 | Jensen ..................... A61F 2/95 623/1.11 |

FOREIGN PATENT DOCUMENTS

| | | |
|---|---|---|
| EP | 1484078 A1 | 12/2004 |
| WO | 96/30072 A1 | 10/1996 |
| WO | 98/18393 A1 | 5/1998 |
| WO | 99/25411 A1 | 5/1999 |

OTHER PUBLICATIONS

Double J Stent; Advin Health Care; Mar. 29, 2016; www.indiamart.com/advinhealthcare/urology-drainage.html; 11 pages.
Chronic Hemodialysis Catheter; Angiodynamics; May 8, 2016; www.angiodynamics.com/uploads/pdf/082714-090225_<:C_035_Schon_RevJ-ipad.pdf; 2 pages.
PTCA Guiding Catheter; Apr. 13, 2016; www.terumo-europe.com/en-emea/interventional-cardiology/coronary-intervention-products/ptca-guiding-catheter/heartrail®-ii-ptca-guiding-catheter; 5 pages.
French Catheter Scale; Feb. 10, 2016; https://en.wikipedia.org/wiki/French_catheter_scale; 3 pages.
International Search Report dated Oct. 10, 2017 for PCT/IB2017/053276 and English translation.

* cited by examiner

HORSESHOE-SHAPED GUIDE CATHETER AND PROCEDURE FOR DUCTUS ARTERIOSUS ANGIOPLASTY IN NEWBORN AND INFANT PATIENTS

CROSS REFERENCE TO RELATED APPLICATION

This Application is a 371 of PCT/IB2017/053276 filed on Jun. 2, 2017 which, in turn, claimed the priority of Colombian Patent Application No. 16-146226 filed on Jun. 3, 2016, both applications are incorporated herein by reference.

The present invention relates to a guide catheter with a specific shape and curvature, which allows access to the ductus arteriosus of newborns and infants with congenital heart disease and duct-dependent pulmonary circulation and the implantation of one or more stents along its length through angioplasty, preserving it open during extrauterine life. The latter, so that the patient can survive during the neonatal and infant period and gain weight until, months later, a corrective surgery can be safely performed with better outcomes.

BACKGROUND OF THE INVENTION

It is estimated that worldwide, around 276,000 newborns die each year during the first four weeks of life due to congenital anomalies [1]. Additionally, heart diseases account for about one-third of these anomalies, thus becoming one of the main causes of mortality, chronic diseases, disability and therefore, complications in childhood [2].

An important group of cardiac malformations are anomalies in which the basic problem is the absence (or defective development) of structures that carry blood in and out of the heart or that impact its correct performance. The most common heart disease that requires the use of the invention described herein, is known as pulmonary atresia and is described below.

Pulmonary Atresia

In this heart disease, the pulmonary heart valve 1 of the fetus does not develop normally and remains blocked even after birth [3]. The pulmonary valve 1 is the structure that separates the right ventricle 2 from the pulmonary artery 3, an artery through which blood normally flows to the lungs to receive oxygen and then is delivered to the rest of the body. When the valve is not present, blood is prevented from flowing from the heart to the lungs, which causes the patient's body to receive deoxygenated blood and thus quickly acquire a blue coloration, known as cyanosis. In this heart disease, the only blood flow to the lungs occurs through the ductus arteriosus 4 (open duct between the pulmonary artery 3 and the aorta 5, see section: Ductus Arteriosus) which is permeable during intrauterine life. However, the fact that the ductus 4 is prone to close a few days after birth, creates a concern for the survival of these newborn patients, whose pulmonary circulation depends on the ductus 4 being kept open during extrauterine life [4], [5], as shown in FIG. 1.

This heart disease usually occurs in different varieties and in combination with other congenital heart diseases, including single ventricle 6, ventricular septal defect 11 and intact ventricular septum 12. In these diseases, the only pulmonary circulation blood flow occurs when part of the blood circulating through the aorta 5 is diverted through the ductus 4 to the lungs, which shows the importance of keeping this communication open.

Single Ventricle with Pulmonary Atresia

This heart disease occurs when there is a single ventricle 6 capable of pumping an adequate amount of blood out of the heart. In this ventricle, oxygenated and deoxygenated blood from the left 7 and right 8 atria, respectively, converge and mix to then flow out from the large arteries in a variable proportion to be delivered to the rest of the body and the lungs [6] (FIG. 2A).

In a patient who presents pulmonary atresia with single ventricle 6, the deoxygenated blood that comes from the right atrium 8 goes to the single ventricle 6, where it is mixed with the oxygenated blood from the left atrium 7. Due to the fact that the passage to the pulmonary artery 3 is blocked, the only way out for the blood that is inside the ventricle is the aorta 5 [6].

Pulmonary Atresia with Ventricular Septal Defect (VSD)

In the initial stage of normal heart development, the fetus' heart has only one ventricle. As the fetus develops, a wall 9 that divides the large ventricle into two is formed, thus generating the two ventricles, left 10 and right 2. This heart disease occurs when there is a hole in this wall 9, which during the growth process is not completely formed, thus allowing communication 11 between the two ventricles [7] (FIG. 2B).

In a patient with pulmonary atresia with ventricular septal defect 11, the deoxygenated blood coming from the right atrium 8 goes to the right ventricle 2 and through the ventricular hole 11, to the left ventricle 10 and to the aorta 5, since there is no passage to the pulmonary artery 3. Blood is ejected from there through the aorta 5 towards the rest of the body [6].

Pulmonary Atresia with Intact Ventricular Septum

This heart disease is characterized by the absence of defects in the wall that separates the ventricles 9 and therefore by a lack of communication between them. In a patient with pulmonary atresia and intact ventricular septum 12, there is no outlet for the deoxygenated blood that reaches the right ventricle 2 from the right atrium 8, which increases the pressure inside the ventricle 2. Part of this blood returns to the right atrium 8 and flows to the left atrium 7 through the interatrial communication 13, where it is mixed with the oxygenated blood. Then, mixed blood goes to the left ventricle 10, and from here, it is ejected into the body through the aorta 5 [6] (FIG. 2C).

Ductus Arteriosus

Around the 8th week of life, the fetus develops a blood vessel known as ductus arteriosus 4, required to enable normal blood flow during the rest of the gestational period [4] (FIG. 1B). The ductus arteriosus is a fetal structure that connects the pulmonary artery 3—through which deoxygenated blood flows from the right ventricle 2 of the heart to the lungs—with the distal portion of the descending aorta 5b, allowing part of the blood ejected by the right ventricle 2 in the fetal circulation to be driven to the aorta 5 [4], [5], [8].

During intrauterine life, gaseous exchange occurs in the placenta and not in the lungs (where it occurs after birth). For this reason, during the gestation period, the lungs are not yet ventilated, but full of fluid, which causes high pulmonary vascular resistance [4], [5]. Since there is no ventilation, a high blood flow through the pulmonary circulation is not required, and only a small amount of blood (5-10% of total ventricular output) is ejected by the right ventricle 2 towards them, thus fulfilling the minimum nutritional and metabolic requirements of these organs [5], [9]. The right ventricle 2 ejects 65% of the total ventricular output, so the remaining 55%, which does not pass through the lungs, is diverted by the ductus arteriosus 4 outside the high resistance pulmonary circulation into the low resistance systemic circulation, particularly towards the umbilical circulation. Thus, without this structure, the high vascular resistance exerted by the fetus' lungs would generate an overload in the right ventricle 2 of the fetus' heart, putting his survival at stake [5].

Typically, the ductus 4, when observed from a frontal view, is angled and straight, joining the aorta 5 with the pulmonary artery 3. Its junction with the aorta 5 (proximal side, 4a) may have a larger diameter than the junction with the pulmonary artery 3 (distal side 4b), thus resulting in a funnel shape.

Recent studies have shown that the forces generated by the flows inside the heart and the vessels during their development process regulate the formation of different structures, including valves, chambers, and ducts [10], [11]. If these flows are not ideal, congenital heart diseases will likely develop, with structures presenting abnormal shapes and configurations [11]. Considering this, many patients with congenital heart disease and pulmonary atresia have been found to have ductus 4 with even more tortuous and abnormal morphologies than patients without heart disease, mostly characterized by the formation of an acute angle between the axis of the descending aorta 5b and the axis of the proximal side of the ductus 4a. FIG. 3 shows some of the possible ductus' 4 morphologies which have been observed in patients with heart diseases.

Some of the factors that keep the ductus arteriosus 4 open during intrauterine life are low partial oxygen pressure inside [18 mmHg] and the local presence, production and circulation of prostaglandins and nitric oxide [4], [5].

At birth, the intravascular environment of the baby changes rapidly; the lungs begin to function and receive greater blood flow, thus reducing the blood pressure exerted by the pulmonary side [4], [5]. This increases the partial oxygen pressure inside the ductus 4, as well as a decrease in the concentration of prostaglandins and nitric oxide, which causes the contraction and the definitive closure of the ductus arteriosus 4 during the first days of extrauterine life [4], [5].

Current Treatments

The most common method used to keep the ductus 4 open in newborns with congenital heart disease dependent on this communication, is the intravenous administration of prostaglandins. However, besides the concerns that arise regarding the effects that prolonged infusion of these drugs can cause in these patients [5], the effect of prostaglandins is lost with age, which has led physicians to look for alternative ways to keep the ductus 4 open and functional, so that the patient can survive during the neonatal period and early infancy and gain weight, before performing one or several corrective surgeries.

One of the current treatment options, besides the administration of prostaglandins, is an initial palliative surgery in which a fistula is created to connect the aorta 5 with the pulmonary artery 3 [12]. This procedure was performed for the first time in 1945 by Dr. Alfred Blalock and Dr. Hellen Taussig [13], [14] and since then, and despite advances in repair techniques for congenital heart diseases and the trend towards primary repair, this is still the most common palliative procedure performed in patients suffering from ductal-dependent congenital heart diseases.4 [15]. The creation of a fistula has proven to be effective and generally, a few months later, it is possible to perform a definitive corrective surgery on the patient. However, in low birth weight infants with severe cardiac malformations, this procedure causes significant morbidity due to the potential post-operative complications [15]. Some of the complications that can compromise repair feasibility are pleural effusion, diaphragmatic paralysis, heart failure due to excessive pulmonary flow and distortion of the pulmonary artery, which leads patients to longer intensive care periods [15].

For some years now, a different, less invasive method has been sought to replace surgical creation of a fistula. One of the most innovative and promising methods so far has been ductal angioplasty 4, in which stents 15—devices that keep vessels open—are placed by catheterization throughout the ductus 4, so as to keep it open in a safe manner and without the need for drugs or creating artificial arteriovenous communications [5], [15]. This procedure is performed through an arterial or venous access, usually in the femoral artery or vein, through which a guide catheter 16 is inserted and advanced up to the ductus lumen 4; then, a catheter for stent delivery 22 can be inserted to release the stents inside the ductus 4, so as to prevent its closure.

Since the ductus 4 is a natural biological structure, one of the main advantages of this new method is that its shape and the blood flow distribution inside it and in the aorta 5 and pulmonary 3 arteries will be more natural and better balanced to both lungs than creating an aortopulmonary fistula.

In the process of creating a fistula a connection is made between the aorta 5 and one of the pulmonary branches 3, which causes blood flow to initially reach one branch and then flow to the other. This causes a flow imbalance between the two lungs, which eventually can cause an undesirable differential growth in the pulmonary arteries [12], [15]. Additionally, ductal angioplasty 4, eliminates the acute complications associated with the thoracotomy required to create the fistula, in addition to the long-term scarring problems, which can cause difficulties when performing definitive repair [15]. Moreover, it eliminates the need for palliative surgery, which optimizes time and reduces the number of operations required for definitive surgical correction [12]. Finally, the cost associated with stent implantation 15 on the ductus 4 is significantly lower than the surgical arteriovenous fistula, including the costs associated with intensive care treatments and hospitalization time for recovery and follow-up [12].

Access to the interior of the ductus from the right carotid artery, the subclavian artery or the axillary artery, usually by open artery surgery are among the recent options for performing the procedure with stents [12]. However, these approaches for stent 15 angioplasty of the ductus 4 are considered an extreme measure, because the carotid arteries carry blood to the brain and the subclavian arteries to the upper limbs. Any complication or anatomical defect secondary to the intervention, using the carotid arteries, can cause greater complications than the approach from the femoral artery or vein described herein, and may even compromise newborn's brain integrity, with life-long consequences.

Different studies have been conducted on the safety, efficacy, medium-term results and complications of stent angioplasty of the ductus arteriosus 4 in patients with ductal-dependent pulmonary circulation [12], [15], and have shown good results. However, they also show that currently, this procedure is only recommended for patients with ductus arteriosus 4 of a certain favorable anatomy, that is, an almost straight geometry, and not tortuous or excessively long. Procedures have failed in patients with an abnormal ductal origin 4, in addition to an excessively tortuous morphology, which prevented the catheter from entering the ductus to position the guidewire and anchor it to the bronchial circulation until the procedure was completed [15].

This shows that there is a technical difficulty when performing this procedure, due to the multiple ductal 4 morphologies in this type of patients and the acute angle formed by the main axis of the proximal ductus 4a and the axis of the descending aorta 5b, which have prevented its standardization as an effective and safe procedure for all the newborns who need it. For this reason, the studies conclude that there is a need to improve the stent designs and their delivery systems, so that this less invasive procedure can be a safe, viable and effective initial palliative option for all patients with a ductal-dependent congenital heart disease 4 and, as an alternative to aortopulmonary shunts [12], [15].

Catheter for Ductus Angioplasty

With medicine developments, treatment techniques tend to be less invasive, and open-heart surgery has been largely replaced by minimally invasive procedures. In this sense, catheters have been used in non-invasive medical procedures for many years. These devices allow doctors to examine, diagnose and perform a procedure at a specific point inside the body, which would otherwise be inaccessible without more invasive procedures [16]. Catheters are usually inserted through a large vein or artery that is located close to the body surface. Once inserted, they are directed to the specific location using the proximal tip and sliding it down inside the artery or vein in which it was originally inserted.

Over the years, catheters have become very useful devices, allowing interventionalists to access remote parts of the body. However, each catheter is specifically designed for the body part being targeted, thus limiting its range of use. In this way, for example, the distal tip of catheters designed to access the right coronary artery differ from that of catheters designed to access the left coronary artery. Catheter design is tailored to the way it is supposed to rest inside the vessels, that is, to successfully access the targeted vessel and reach the specific point inside the body for which it was designed. Therefore, there are currently a large number of patents that describe catheters with predetermined shapes, designed to be used in specific procedures.

The size, shape, internal configuration, function and orientation of the human heart changes significantly from birth to adulthood. Due to these differences between adult and pediatric hearts, all devices used in pediatric hearts should have a different shape and size than those used to treat adult hearts. However, diagnose and treatment catheters have historically been developed for adult heart diseases, and their use in pediatric patients extends simply by reducing its size and profile, without modifying their design.

Furthermore, congenital heart malformations in newborns cause heart structures to differ from those of adult hearts and currently there are very few catheters that would allow to treat them.

The lack of a specific catheter to enter the ductus arteriosus 4 in newborns has forced interventional cardiologists to perform angioplasty of the ductus arteriosus 4 with catheters available on the market, which are not originally designed for this purpose. In these cases, the catheter to be used is selected based on the ductus 4 geometry of the specific patient who will undergo the procedure [12], [15]. Some of the commercial catheters that have been used to perform this procedure in different studies [12], [15] include 4F Pigtail angiography catheter, 4F Cobra catheter (Cordis), right or left Judkins coronary catheter (Cordis) or multipurpose catheter (Cordis) [12], [15]. However, none of these catheters and none of the catheters available in the market have the geometry and shape required for its tip to enter the lumen of any ductus arteriosus. Thus, none of them allow to perform the stent angioplasty in all newborns with congenital heart diseases and ductal-dependent pulmonary circulation 4, regardless of the geometry and tortuous nature of the communication. Likewise, only some of them have the lumen required to be a guiding catheter, through which a new catheter can be inserted to place stents of the desired reference inside the ductus.

Therefore, the present invention aims to provide a guide catheter to perform stent angioplasty 15 of the ductus arteriosus 4 in newborn patients with congenital heart disease, whose pulmonary circulation depends on the persistence of this communication, so as to standardize this procedure in all patients with this diagnosis as the initial palliative procedure of choice, after which the patient can undergo corrective surgery as the first surgical intervention [12].

SUMMARY OF THE INVENTION

The present invention relates to a horseshoe-shaped guide catheter 16 whose shape, size, and geometry make it especially suited to access all types of ductus arteriosus 4 (regardless of their shape) in newborn and infant patients with severe ductal-dependent heart diseases.

As a guiding catheter, it enables a catheter 22, stent carrying catherer 15, to be inserted to release the catheters into the ductal 4 and allow their expansion along the ductus 4 so as to keep the communication and prevent its closure. This guiding catheter 16 is precurved in a specific horseshoe shape, designed so as to correctly fit the ductus 4a morphology at the aortic end and to rest on the wall opposite the origin of the ductus 4, so that the tip of the catheter is hooked (coupled) to it and the catheter 16 can enter its lumen to enable the rest of the procedure. This specific shape allows the catheter 16 to reach the ductus arteriosus 4 and pass through its proximal end 4a when entering through the aorta 5.

The invention also includes the procedure by which the horseshoe-shaped catheter 16 enables stent 15 angioplasty of the ductus arteriosus 4 in any newborn patient with severe heart diseases and ductal-dependent 4 pulmonary circulation.

DETAILED DESCRIPTION OF THE INVENTION

The horseshoe-shaped guide catheter 16 is a long tube with a circular cross-section, comprising mainly of two sections with different geometric preshapes. Both sections are part of the catheter and there is no marked physical division between them. However, both sections are described separately so as to better illustrate the overall shape of the catheter.

Figure 1A:
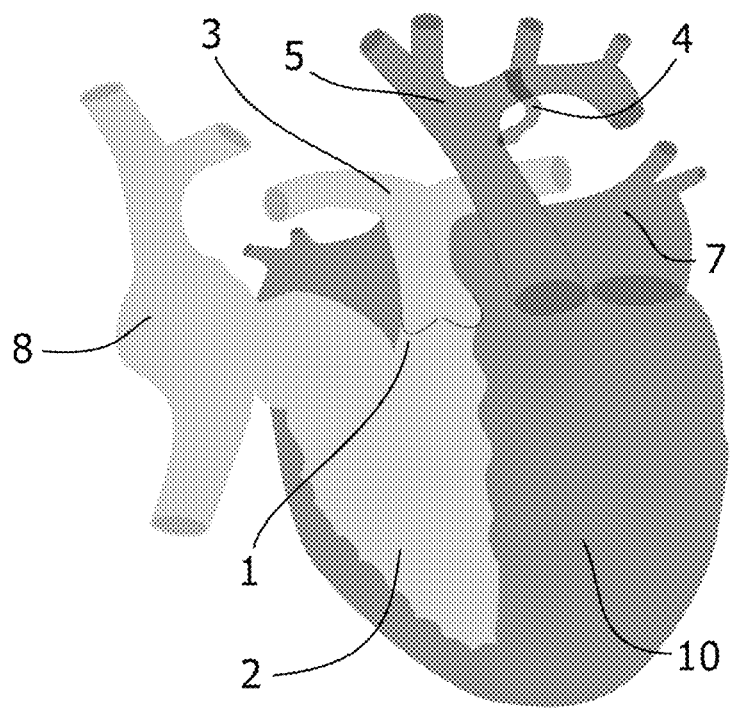
FIG. 1A shows a diagram of a healthy heart where all the heart and vessel structures relevant to the invention's description and use are pointed out.
Figure 1B:
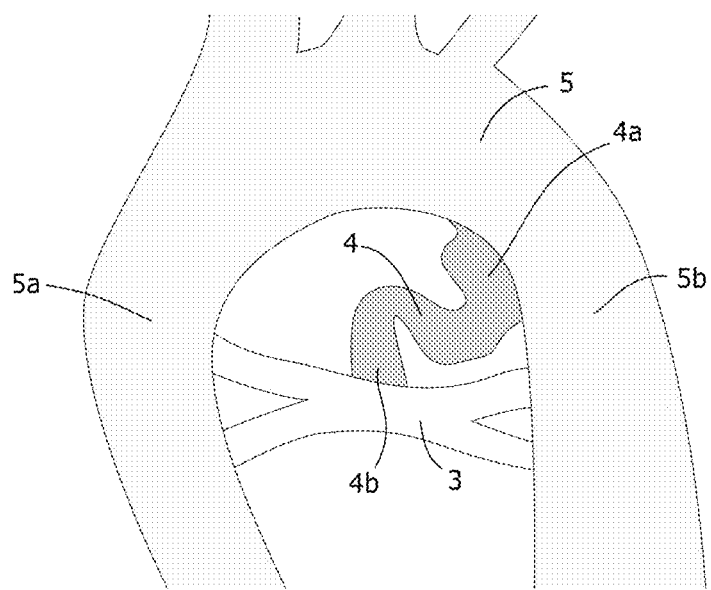
FIG. 1B shows a diagram of a zoomed in view on the aorta 5 and pulmonary artery 3 which are communicated through the ductus arteriosus 4.
Figure 2A:
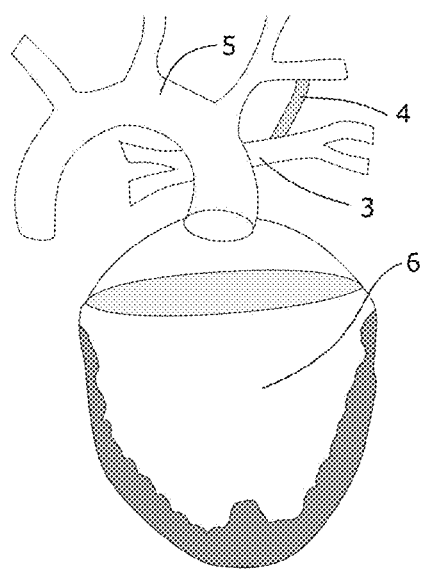
FIG. 2A shows a diagram of a heart with pulmonary atresia and single ventricle 6.
Figure 2B:
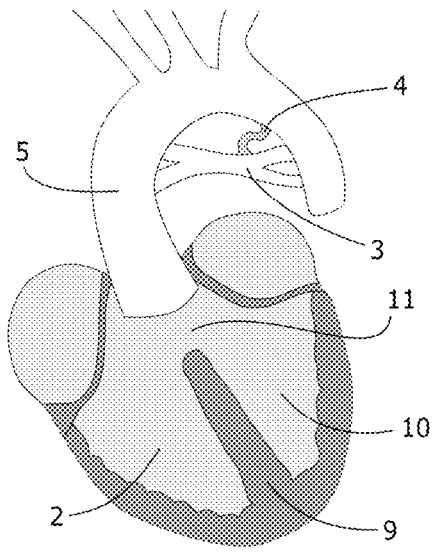
FIG. 2B shows a diagram of a heart with pulmonary atresia and ventricular septal defect 11.
Figure 2C:
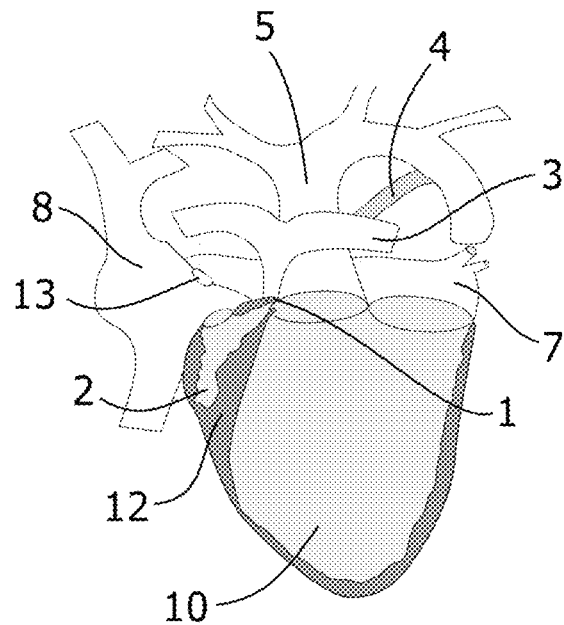
FIG. 2C shows a diagram of a heart with pulmonary atresia and intact ventricular septum 12.
Figure 3:
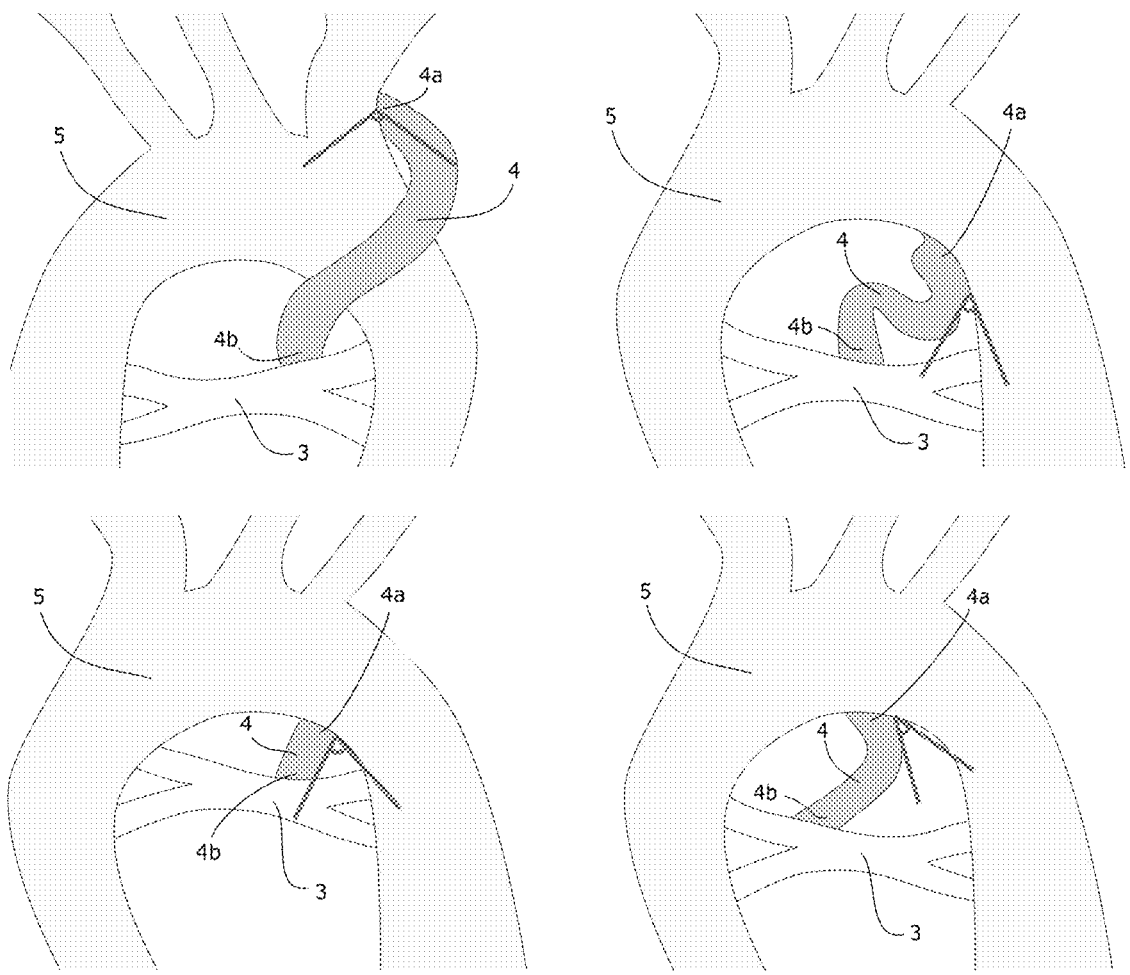
FIG. 3 shows a diagram of different ductal 4 morphologies observed in patients with pulmonary atresia and the acute angle generally formed between the axis of the descending aorta 5b and the axis of the ductal proximal side 4a in newborns with pulmonary atresia. This angle is one of the key features in the geometry of the ductus 4, which hinders accessibility with current proprietary and commercial catheters.
Figure 4:
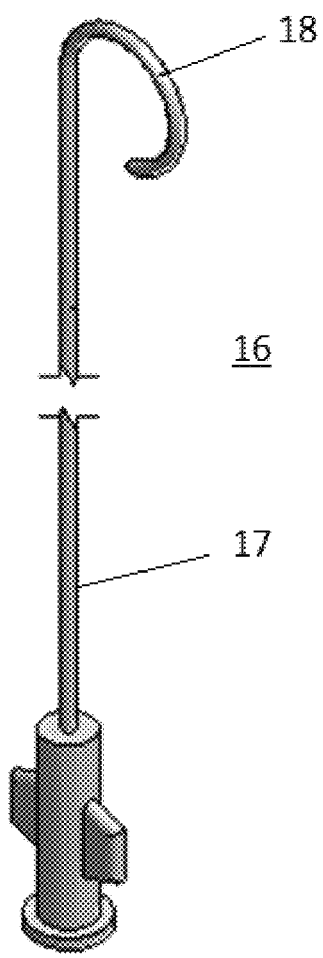
FIG. 4 shows an isometric view of the proposed guide catheter 16 showing the shape of the distal tip 18.
Figure 5:
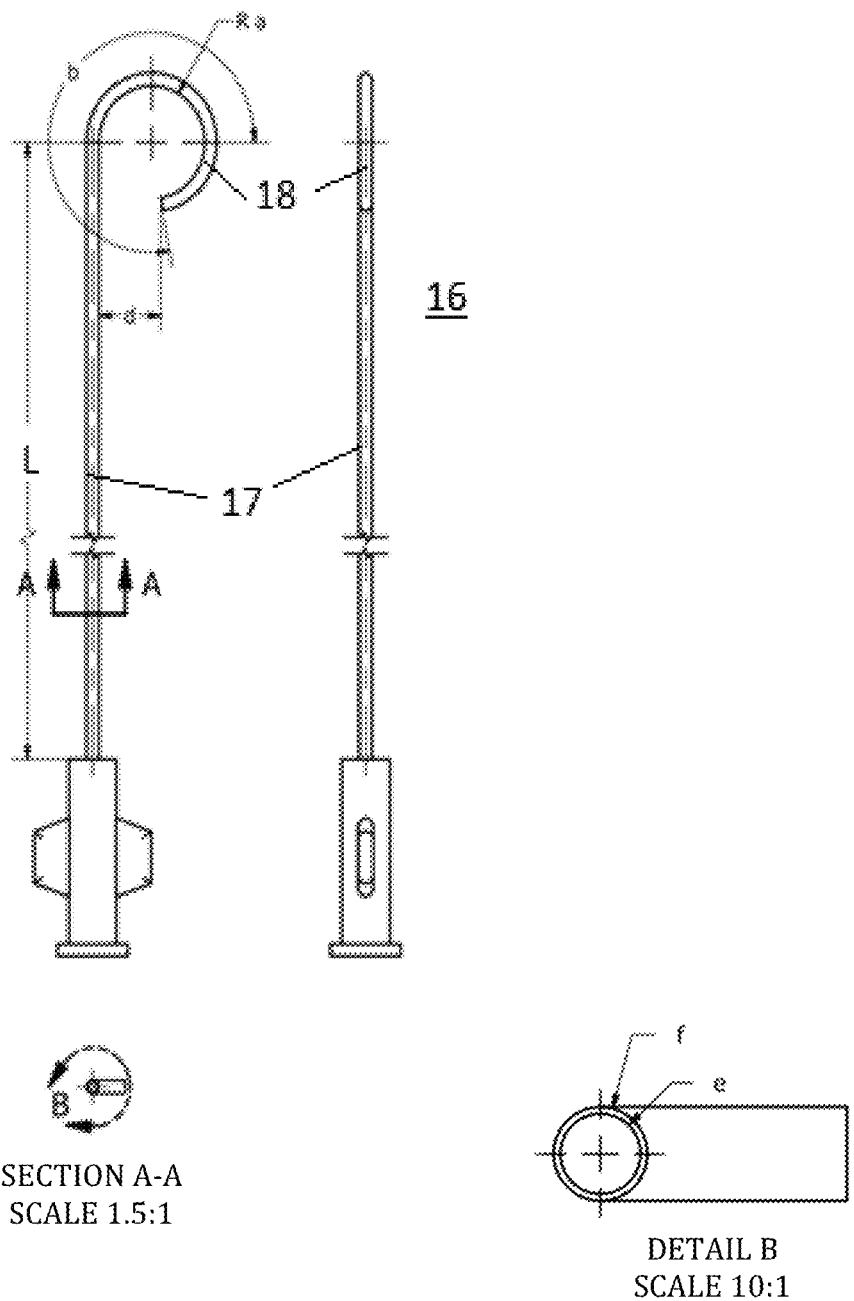
FIG. 5 shows the front and lateral view of the proposed guide catheter 16. A cross-sectional view of the proposed catheter is also provided with detail on inner and outer diameters.

The first section of the guide catheter 17 is a long, straight conventional section, long enough to be inserted in the patient and be handled from the insertion point towards the targeted heart point during the procedure. This catheter is intended for pediatric patients; therefore, the total length in the straight section (see "L", FIG. 5) ranges between 55 and 65 cm, preferably, 55 cm.

Connected to the first section of the guide catheter, there is a second section 18 comprising a curved portion shaped as a circle section. This portion has a radius (see "R a", FIG. 5) of 7.5-9 mm (preferably, 9 mm) with an arc (see "b", FIG. 5) of 180-280° (preferably, 270°). The distance between the tip and the straight part of the catheter without deformations (see "d", FIG. 5) is 7-15 mm (preferably, 7 mm).

The inner diameter or lumen of the catheter (see "e", FIG. 5) can range between 1.42-1.65 mm (0.056-0.065 inches) so as to enable a stent-carrying catheter 15 to be advanced inside it (and which are able to expand from 3 mm up to 4 mm as final diameter), preferably, 1.5 mm (0.059 inches). Likewise, the outer diameter of the catheter 16 (see "f", FIG. 5) can range between 4 (1.35 mm) and 5 "French" (F) (1.67 mm), so as to enable the catheter 16 to go through the small vessels of the newborn and reach the ductus 4, without damaging them, preferably 4 F (1.35 mm).

The guide catheter 16 can be made of any shape-memory polymeric material suitable for human use, so as to allow the catheter to return to its original three-dimensional shape once it has been manipulated and deformed after being inserted in the patient. Furthermore, the polymeric material must be rigid enough to allow the interventionalist to handle and guide it through the vessels until it reaches the ductus arteriosus 4 without damaging the arteries, veins or organs.

While the previously described shape is preferred, the sections of the catheter can be modified as long as the shape and general dimensions of the catheter are close to those described herein and meet the aforementioned specifications.

Detailed Description of the Procedure Used with the Proposed Catheter

The ductus arteriosus angioplasty 4 with stents 15, can be performed according to the conventional angiography procedure, combined with some methods and instruments currently used in medical practice for placing this type of devices. The procedure is performed with the patient under general anesthesia and the preferred route of access is retrograde through the femoral artery. However, the procedure can also be performed with an antegrade approach by the femoral vein, accessing the ascending aorta 5a through the interventricular communication 11 or through the single ventricle 6, when present. The complete procedure is described below, as well as the possible variations of the method.

Figure 6A:
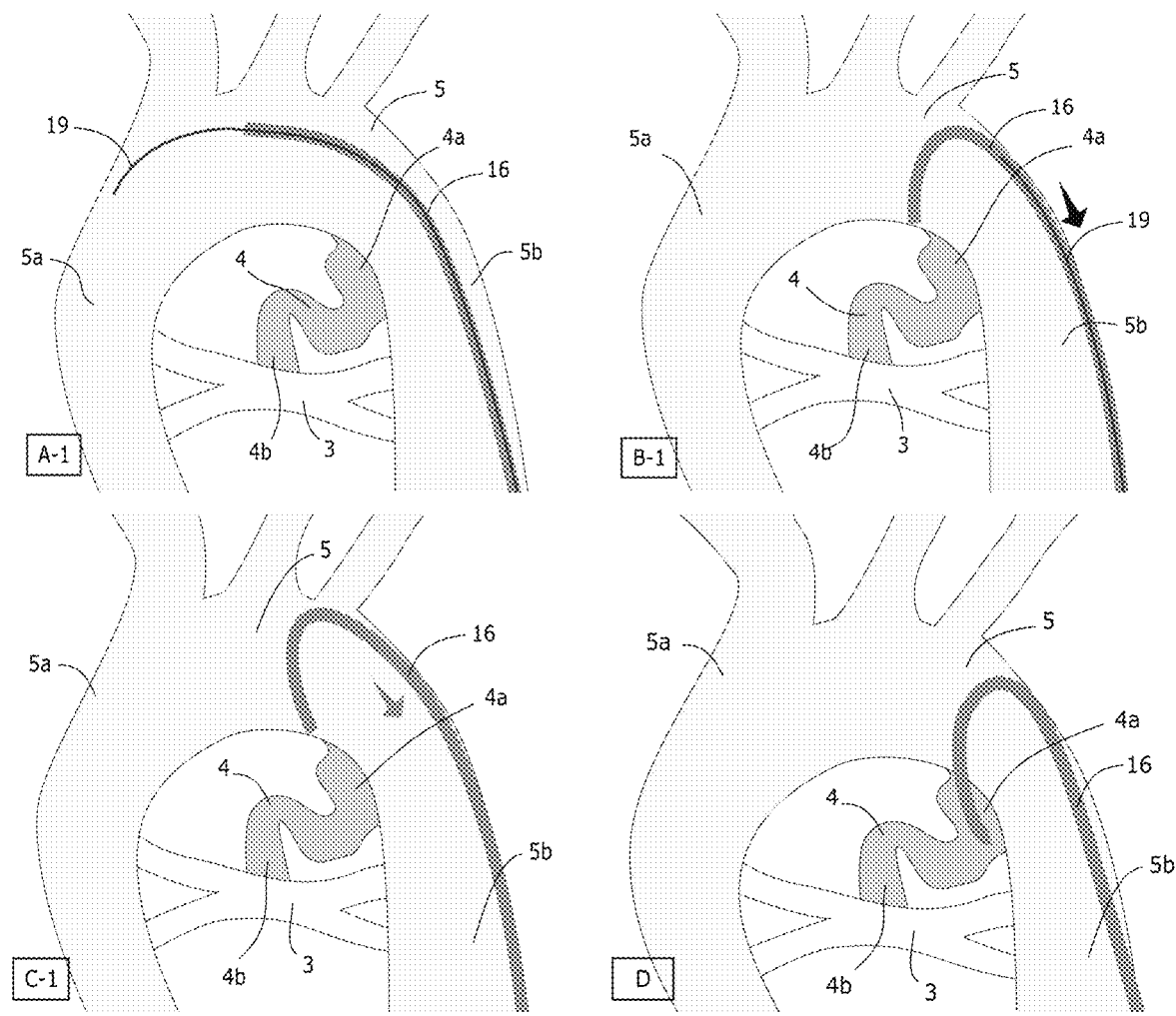
FIG. 6A shows the process of insertion of the catheter inside the ductus arteriosus 4 after reaching the aorta 5. Images A-1, B-1, C-1, and D describe how to handle the catheter 16 if its tip goes beyond the origin of the ductus 4 when entering the aorta 5.
Figure 6B:
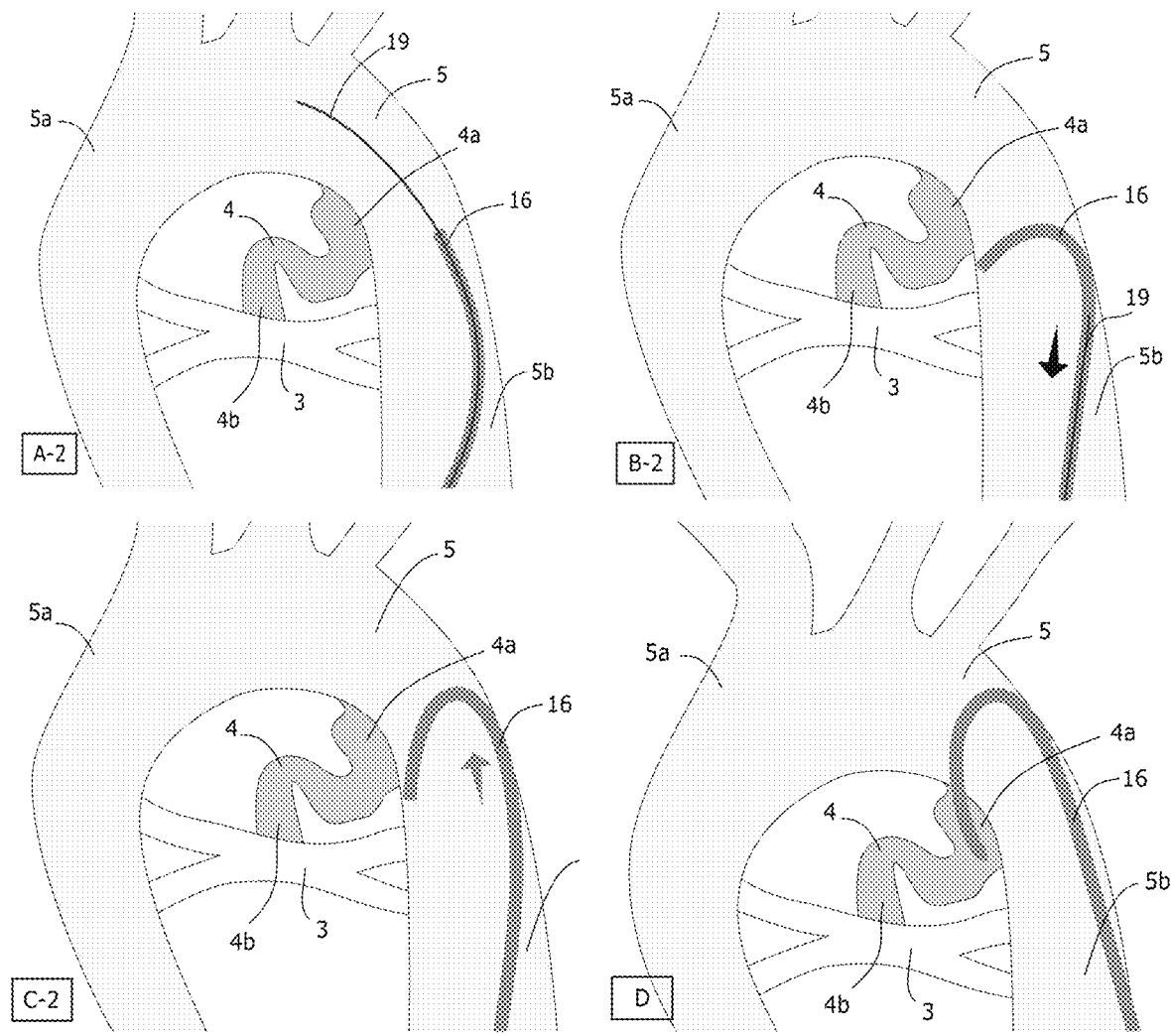
FIG. 6B shows the process of insertion of the catheter inside the ductus arteriosus 4 after reaching the aorta 5. The images A-2, B-2, C-2, and D describe how to handle the catheter 16 if its tip has not yet gone beyond the origin of the ductus 4.
Figure 7:
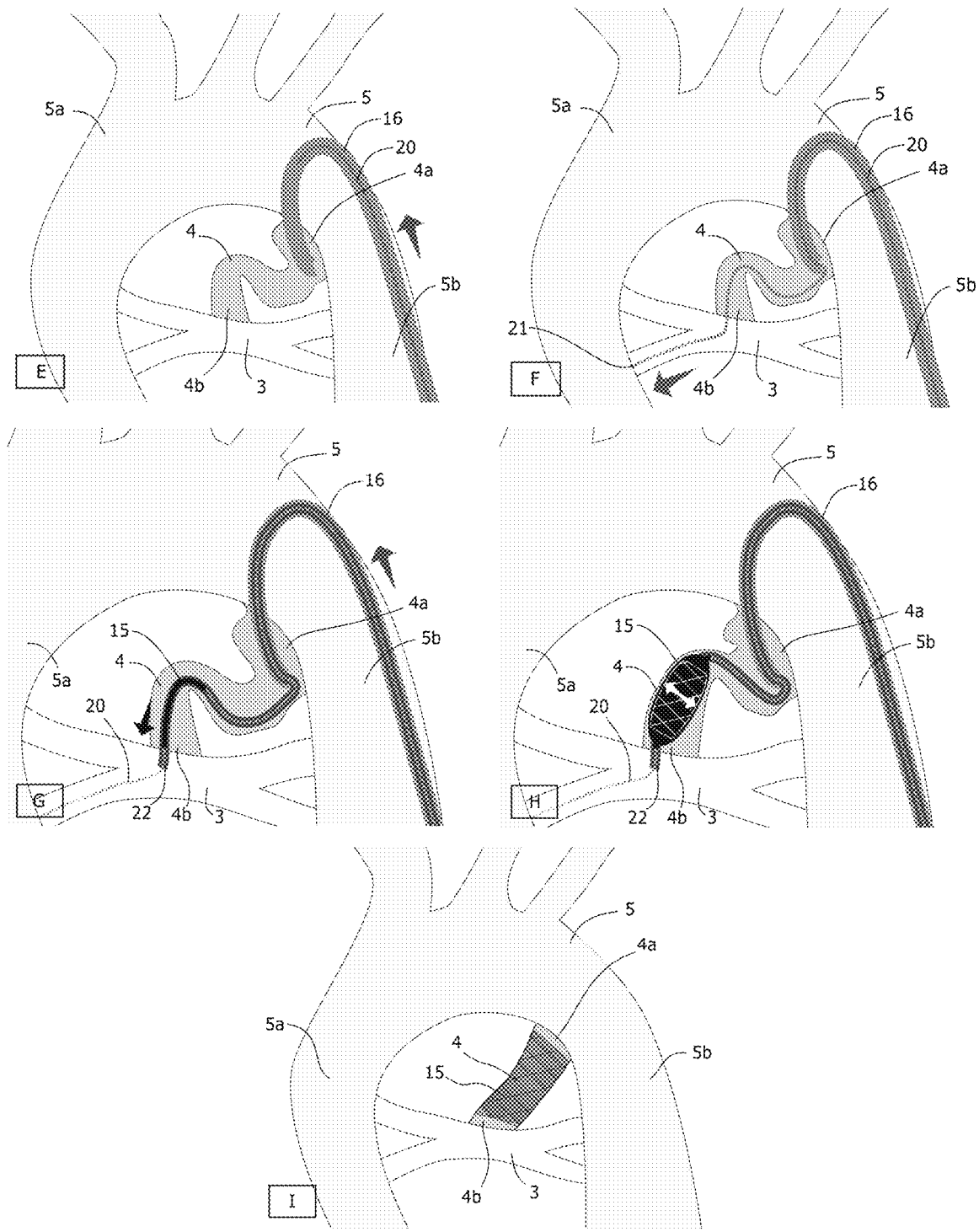
FIG. 7 shows steps E-I, which must be followed once the catheter 16 is inside the ductus 4 to perform the angioplasty procedure.

1. First, the horseshoe-shaped guide catheter 16 is inserted with an angiographic guidewire 19, preferably of 0.89 mm (0.035 inches) through the femoral artery or through the femoral vein up to the aorta 5 and until the catheter's tip 16 has gone beyond the origin of the ductus 4 (FIG. 6.A-1) or is lodged in its proximity (FIG. 6.A-2) on its aortic side 4a.
2. Then, the guidewire 19 is withdrawn from inside the catheter 16, in such a way that the distal end section 18 of the horseshoe-shaped catheter acquires its curved shape and rests on two points of the aorta 5, namely, the aortic wall opposite to the junction between the aorta and the ductus arteriosus 4a, and the adjacent wall to the junction 4a (see FIGS. 6.B-1 and 6.B-2).
3. Slide the catheter 16 upwards in such a way that this movement causes it to bend even more and firmly rest on the two points mentioned above.
4. Slide the horseshoe-shaped catheter 16 downwards (see FIG. 6.C-1) or upwards (see FIG. 6.C-2) so that its tip enters the origin of the ductus arteriosus 4a (see FIG. 6.D).
5. Advance a new floppy guidewire 20, preferably of 0.36 mm (0.014 inch) inside the horseshoe-shaped catheter 16 (see FIG. 7.E), and using the blood flow, make the floppy guidewire travel the total length of the ductus and enter the pulmonary artery 3 until it is firmly attached to a distal pulmonary artery 21 (see FIG. 7.F), thus avoiding its release during the next steps of the procedure.
6. Using the new guidewire 20, advance a catheter 22 carrying stents 15 through the horseshoe-shaped catheter 16 with a preferred final diameter of 3-4 mm (see FIG. 7.G).
7. Expand the stents 15 from the pulmonary distal end of the ductus (distal end, 4b) to the end connected to the aorta 5 (proximal end, 4a) (see FIG. 7.H), until the ENTIRE ductus 4 is covered with stents 15 (see FIG. 7. I). The implanted stents 15 should protrude from the ductus at both ends by about 2-3 mm.

It should be stressed that if any area of the ductus 4 is not covered by stents 15, it can become narrow and occlude the ductus 4, thus requiring a new procedure. Likewise, it should be noted that the ductus arteriosus 4 is very sensitive to handling and may be closed. If the procedure fails on the first attempt, there might very well not be a second opportunity to keep it open.

BIBLIOGRAPHY

[1] «OMS|Anomalías congénitas», WHO. [En línea]. Disponible en: http://www.who.int/mediacentre/factsheets/fs370/es/. [Accedido: 28-dic-2015].
[2] «WHO|Causes of child mortality», WHO. [En línea]. Disponible en: http://www.who.int/gho/child_health/mortality/causes/en/. [Accedido: 28-dic-2015].

[3] «Atresia pulmonam. [En línea]. Disponible en: http://www.heart.org/HEARTORG/Conditions/Congenital-HeartDefects/AboutCongenitalHeartDefect s/Atresia-pulmonar_UCM_447863_Article.jsp#.VoCx3OPhCRs. [Accedido: 28-dic-2015].

[4] D. J. Schneider, «The Patent Ductus Arteriosus in Term Infants, Children, and Adults», *Semin. Perinatol.*, vol. 36, no. 2, pp. 146-153, abr. 2012.

[5] V. Gournay, «The ductus arteriosus: Physiology, regulation, and functional and congenital anomalies», Arch. Cardiovasc. Dis., vol. 104, no. 11, pp. 578-585, November 2011.

[6] «CardioCongénitas: cardiopatias congénitas», *Cardiocongenitas*. [En línea]. Disponible en: https://cardiocongenitas.com.ar/. [Accedido: 28-dic-2015].

[7] «Comunicación interventricular: MedlinePlus enciclopedia médica». [En línea]. Disponible en: https://www.nlm.nih.gov/medlineplus/spanish/ency/article/001099.htm. [Accedido: 28-dic-2015].

[8] A. Sehgal y P. J. McNamara, «The Ductus Arteriosus: A Refined Approach!», *Semin. Perinatol.*, vol. 36, no. 2, pp. 105-113, abr. 2012.

[9] J. Nair y S. Lakshminrusimha, «Update on PPHN: mechanisms and treatment», *Semin. Perinatol.*, vol. 38, no. 2, pp. 78-91, March 2014.

[10] V. Menon, J. F. Eberth, R. L. Goodwin, y J. D. Potts, «Altered Hemodynamics in the Embryonic Heart Affects Outflow Valve Development», *J. Cardiovasc. Dev. Dis.*, vol. 2, no. 2, pp. 108-124, 2015.

[11] S. V. Biechler, L. Junor, A. N. Evans, J. F. Eberth, R. L. Price, J. D. Potts, M. J. Yost, y R. L. Goodwin, «The impact of flow-induced forces on the morphogenesis of the outflow tract», *Front. Physiol.*, vol. 5, p. 225, 2014.

[12] M. Matter, H. Almarsafawey, M. Hafez, G. Attia, y M.-M. Abuelkheir, «Patent Ductus Arteriosus Stenting in Complex Congenital Heart Disease: Early and Midterm Results for a Single-Center Experience at Children Hospital, Mansoura, Egypt», *Pediatr. Cardiol.*, vol. 34, no. 5, pp. 1100-1106, June 2013.

[13] «Tetralogy of Fallot—Surgery». [En línea]. Disponible en: http://pediatricheartspecialists.com/articles/detail/tetralogy_of_fallot_surgery. [Accedido: 28-dic-2015].

[14] Blalock A y Taussig H B, «The surgical treatment of malformations of the heart: In which there is pulmonary stenosis or pulmonary atresia», *JAMA*, vol. 251, no. 16, pp. 2123-2138, abr. 1984.

[15] M. Alwi, K. K. Choo, H. A. Latiff, G. Kandavello, H. Samion, y M. D. Mulyadi, «Initial results and medium-term follow-up of stent implantation of patent ductus arteriosus in duct-dependent pulmonary circulation», *J. Am. Coll. Cardiol.*, vol. 44, no. 2, pp. 438-445, July 2004.

[16] R. C. Diggery y D. T. Grint, *Catheters: Types, Applications and Potential Complications*. Nova Science, 2011.

The invention claimed is:

1. A method for performing stent angioplasty of the ductus arteriosus by inserting a guide catheter, using a retrograde access through a femoral artery, comprising the steps of:
   i) inserting the catheter with a guidewire through the femoral artery up to the aorta and until a tip of the catheter has gone beyond the start of the ductus or is close to it on its aortic side;
   ii) withdrawing the guidewire from inside the catheter so that a distal end section of the catheter acquires its curved form and rests on two points of the aorta, namely, the aortic wall opposite to the junction between the aorta and the ductus arteriosus, and the adjacent wall to the junction;
   iii) sliding the catheter upwards and causing the catheter to bend even more and firmly rest on the two points of the aorta previously mentioned;
   iv) sliding the catheter downwards or upwards so that its tip enters the lumen of the ductus arteriosus;
   v) advancing a floppy guidewire inside the catheter and with aid of blood flow, making the floppy guidewire travel the total length of the ductus and enter the pulmonary artery until firmly attached to a distal pulmonary artery avoiding its release during the next steps of the procedure;
   vi) using the floppy guidewire, advancing a stent-carrying catheter through the lumen of the guide catheter;
   vii) expanding the stents from the pulmonary distal end of the ductus to the proximal aortic end of the ductus, until the entire ductus is covered with stents,
   wherein the guide catheter has a curved section at the distal end of the catheter rest on an external arch of the aortic wall, the tip of the guide catheter slides on an internal arch of the aortic wall until finding the aortic ductal ostium such that the guide catheter accesses the ductus and allows the stent carrying catheter loaded with stents to perform ductal stent angioplasty.

2. The method of claim 1, wherein the guidewire used in step i) has a diameter of 0.89 mm (0.035 inches).

3. The method of claim 1, wherein the floppy guidewire used in steps v) and vi) has a diameter of 0.36 mm (0.014 inches).

4. The method of claim 1, wherein the stents have a diameter in the range of 3 to 4 mm.

\* \* \* \* \*